United States Patent [19]

Ortega et al.

[11] Patent Number: 5,049,586
[45] Date of Patent: Sep. 17, 1991

[54] VALPROIC ACID TABLETS

[75] Inventors: Aracelis M. Ortega; Pilar M. de Perez, both of Caracas, Venezuela

[73] Assignee: Farvalsa/AG, Zug, Switzerland

[21] Appl. No.: 517,620

[22] Filed: May 2, 1990

Related U.S. Application Data

[63] Continuation of Ser. No. 76,634, Jul. 22, 1987, abandoned.

[51] Int. Cl.$^5$ ............... A61K 9/20; A61K 31/195; A61K 31/19
[52] U.S. Cl. ............................. 514/557; 514/558; 424/465
[58] Field of Search ............... 514/557, 558; 424/465, 424/80

[56] References Cited

FOREIGN PATENT DOCUMENTS 0230332 7/1987 European Pat. Off.

OTHER PUBLICATIONS

Derwent Abstracts, AN 87-061184/09 "Pharmaceutical Antifungal Composition", Japanese Patent J62016431, 1-24-87.
Derwent Abstracts, AN 82-10967E/06, "Mgf. Solid Therapeutic Composition", Japanese Patent J56169622, 12-26-81.
Derwent Abstracts, AN 87-140906/20, "Sodium Valproate Contg. Slow Release Tablets", Japanese Patent J62081309, 4-14-87.
Derwent Abstracts, AN 87-207614/30, "Sustained Release Pharmaceutical Tablets", Finland Patent FI 8,700,092, 7-14-87.

Primary Examiner—Frederick E. Waddell
Assistant Examiner—Diane Gardner
Attorney, Agent, or Firm—Theresa M. Gillis

[57] ABSTRACT

A moisture stable solid valproic acid formulation is provided. The formulation comprises:
- 55 to 65 weight percent valproic acid,
- 10 to 25 weight percent fillers,
- 10 to 20 weight percent disintegrants,
- 3 to 6 weight percent binders, and
- 0.5 to 1.2 weight percent lubricants A preferred formulation is:
- 60 weight percent of valproic acid,
- 20 weight percent of magnesium oxide,
- 15 weight percent corn or potato starch,
- 3 weight percent polyvinylpyrrolidone,
- 1 weight percent sodium carboxymethylcellulose,
- 0.8 weight percent magnesium stearate.

The formulations are manufactured by mxing an alcohol solution of valproic acid with the fillers, drying and then milling the mixture, adding the disintegrants and wet granulating with at least a portion of the binder. The wet granulate is dried, sized and to it is added the lubricant and any remaining binder.

The lubricated granulate can be compressed into tablets without a protective coating.

9 Claims, No Drawings

VALPROIC ACID TABLETS

This is a continuation of application Ser. No. 076,634, filed July 22, 1987, now abandoned.

BACKGOUND OF THE INVENTION

1) Field of the Invention valproic acid, which is a liquid, into solid pharmaceutical form, in particular tablets. The formulations of the invention provide valproic acid in a solid, moisture-stable form without resort to protective coatings.

2) State of the Art

Valproic acid or its salts have known utility as anticonvulsants. However, a number of problems are associated with formulating them in solid form.

Valproic acid is disclosed in U.S. Pat. No. 3,325,361. According to the Merck Index it is a liquid having anticonvulsant and antiepileptic activity. As a liquid it suffers from the difficulty attendant any liquid formulation; that is, it is inconvenient to use since the precise volume necessary to result in administration of the proper dose must be measured for each administration and it is less easily portable than solid dosage forms.

Efforts have been made to address the problems of administering valproic acid by converting it to its salt forms. However, as noted in U.S. Pat. No. 4,301,176, the sodium salt of valproic acid is hygroscopic, therefore precluding production of a compacted tablet formulation. This patent suggests resort to calcium valproate as a chewable tablet to overcome the problems associated with tabletting sodium valproate.

In U.S. Pat. No. 4,558,070 the liquid form of valproic acid and the hygroscopic character of the sodium salt are again noted as limiting the utility of these materials as oral dosage forms. In that patent a stable non-hygroscopic compound is made by combining equimolar amounts of the acid and its sodium or calcium salt to form an oligomer.

The present invention provides valproic acid as a moisture-stable, solid formulation capable of being compressed into tablets.

SUMMARY OF THE INVENTION

This invention relates to a moisture-stable solid valproic acid formulation and to the manufacture of such a formulation. The formulation comprises (amounts stated as weight percent):

| Valproic acid | 55 to 65 |
| Filler | 10 to 25 |
| Disintegrant | 10 to 20 |
| Binder | 3 to 6 |
| Lubricant | 0.5 to 1.2 |

A preferred composition comprises (amounts by weight percent):

| Valproic acid | 60 ± 5 |
| Magnesium oxide | 20 ± 5 |
| Corn starch | 15 ± 1 |
| Polyvinylpyrrolidone | 3 ± 0.2 |
| Sodium carboxymethylcellulose | 1 ± 0.4 |
| Magnesium stearate | 1 ± 0.2% |

The compositions are formulated as follows: Valproic acid is mixed with a solvent, preferably ethyl alcohol. The filler is added with mixing and the resulting mass is dried and then milled. The disintegrant is then added with mixing. The resulting mixture is wet granulated with a solution of the binder. The granules are dried and sized. Lubricants, optionally along with additional disintegrant and/or binder, are then mixed with the dried granules. The resultant lubricated mixture may be compressed into tablets or placed in capsules in amounts appropriate to a unit dosage—commonly less than 500 mg per tablet or capsule.

DETAILED DESCRIPTION OF THE INVENTION

By means of the invention valproic acid can be formulated into a dry, non-hygroscopic powder. The powder is suitable for use in forming compacted tablets or for filling capsules. No protective coatings or other special packaging or protective measures are required to maintain the stability of the formulation against moisture.

The formulation contains valproic acid, fillers, disintegrants, binders and lubricants. As stated above the materials are most commonly formulated into the compositions of the invention in the following proportions:

55 to 65 weight percent valproic acid
10 to 25 weight percent fillers
10 to 20 weight percent disintegrants
3 to 6 weight percent binders
0.5 to 1.2 weight percent lubricants Fillers useful in the invention include a clay or an alkaline earth metal oxide. Examples of fillers are magnesium oxide, aluminum oxide, zinc oxide, magnesium and aluminum silicates, and amorphous silicon oxide. The preferred filler is magnesium oxide. It is preferred that the filler be present at a 15-20 weight percent level.

Disintegrants are present in the formulation to facilitate disintegration in the stomach. Polysaccharides, such as corn and potato starch, dextrins and sugars, which swell thereby promoting disintegration are preferred. Preferred disintegrants are corn or potato starch, preferably at levels of 10 to 20 weight percent. Corn starch at a level of 15 weight percent is most preferred.

Binders used in the formulation are preferably water soluble hydrophilic gel forming polymers. Hydrophilic cellulose gums such as methylcellulose and carboxymethylcellulose, polyvinylpyrrolidone and xanthan gum are suitable binders. The preferred binder is a combination of polyvinylpyrrolidone and sodium carboxymethylcellulose.

These binders are preferably combined in a 3:1 ratio and the combination is preferably present in the formulation at a level of 3 to 6 weight percent.

Lubricants which are useful include talc USP, fatty acids and salts of fatty acids. Specific lubricants include stearic acid and magnesium stearate. In preferred practice magnesium stearate is used at a level of 0.5 to 1.2 weight percent. The most preferred level of lubricant is 0.8 percent.

As an example of the manufacture of the formulation of the invention, the preferred formulation set forth above may be made as follows. The ingredients are used in the following proportions by weight: valproic acid, 500 parts; magnesium oxide, 140 parts; ethyl alcohol, 100 parts; corn starch, 122 parts; polyvinylpyrrolidone, 25 parts; sodium carboxymethylcellulose, 5 parts; and magnesium stearate, 5 parts.

The valproic acid is mixed with the ethyl alcohol (optimally in a 5:1 ratio). The magnesium oxide is added only while stirring, preferably with a planetary mixer. The wet mass produced is dried, for example, at 50° C. in an oven for 16 hours. The dried material is milled, preferably by means of a mesh screen, most preferably a 16 or 32 mesh screen. To the milled mixture, the corn starch is added with mixing, preferably by means of a high sheer mixer. The mixture is wet granulated with 25% polyvinylpyrrolidone solution in ethyl alcohol. The granules are dried, by way of example, in an oven at 60° C. for 10 to 12 hours.

The dried granules are sized, preferably by means of a 16 mesh screen. The sodium carboxymethylcellulose and magnesium stearate, optimally with some corn starch, are added and mixed, for example in a V-blender for ten minutes.

The resulting lubricated granulation can be formed into stable solid unit dosage forms. For example, the granulation can be placed in gelatin capsules or it can be compacted into tablets. The amount of material used in each tablet or capsule is dependent on the dosage desired. As a rule, unit dosage forms contain less than 500 mg per tablet. Dosage levels and schedules would be in accordance with known practice. The formulation is moisture stable and needs no protective coating.

The following examples are illustrative of the invention.

EXAMPLE

Example I

Manufacture 26 kg of valproic acid was mixed with 5 kg ethyl alcohol. 7.5 kg magnesium oxide was then slowly added while mixing with a planetary mixer. The wet mass was transferred to trays and dried in an oven at 50° C. for 16 hours. The dried materials were sized through a 30 mesh screen and then transferred to a high shear mixer. 6.4 kg corn starch was added with five minutes mixing. The resultant mixture was wet granulated with 5.2 kg of a 25% solution of polyvinylpyrrolidone in ethanol. Mixing was effected for 10 minutes The wet mass was dried in an oven at 60° C. for 12 hours The dried granulation was sized through a 16 mesh sieve and transferred to a V-blender. 0.25 kg sodium carboxymethylcellulose and 0.25 kg magnesium stearate were added with mixing for fifteen minutes.

The resulting lubricated granulation was compressed using a conventional tablet press to a tablet hardness within the range of 6 to 8 gk (Schlenniger hardness tester). The foregoing batch provides one hundred thousand 250 mg or fifty thousand 500 mg valproic acid tablets. The granulation can be filled into hard gelatin capsules in the alternative.

Example II

Stability

Tablets manufactured in accordance with Example 1 were stability tested at normal and drastic temperature and humidity conditions. The tablets were packaged in PVC blisters and then stored under three different conditions:

45° C. dry oven
37° C. and 75% R.H.
25°-28° C. (room temperature)

Periodically the tablets were tested for physical appearance, physico-chemical properties and valproic acid content.

The following table shows the valproic acid content as percentage of labeled amount after storage for 6 months in drastic conditions and for three years at room temperature:

| Time (months) | 45° C. | 37° C./75% R.H. | Room Temperature |
|---|---|---|---|
| 0 | 100.0 | 100.0 | 100.0 |
| 3 | 100.0 | 99.2 | 100.1 |
| 6 | 95.6 | 95.3 | 100.5 |
| 12 | — | — | 97.3 |
| 24 | — | — | 97.6 |
| 36 | — | — | 97.2 |

The tablets disintegration time upon stability testing was as follows:

| Time (months) | Disintegration time (minutes) | | |
|---|---|---|---|
| | 45° C. | 37° C./75% R.H. | Room Temperature |
| 0 | 25 | 25 | 25 |
| 3 | 35 | 35 | 25 |
| 6 | 35 | 35 | 25 |
| 12 | — | — | 26 |
| 24 | — | — | 25 |
| 36 | — | — | 20 |

Example III

Bioavailability

Valproic acid 500 mg tablets prepared according to Example I were tested for bioavailability in a random crossover dosing study, using valproic acid syrup as a control and comparing with commercially available sodium valproate enteric coated tablets.

Nine healthy adult volunteers aged 18 to 35 years old were selected for the experiment. The products were randomly administered to the fasted subjects at a dose equivalent to 500 mg of valproic acid. Blood samples were withdrawn at 0.25, 0.50, 0.75, 1, 1.5, 2, 3, 4, 6, 8, 10, 12, 25 and 36 hours after dosing. A waiting period of one week was allowed between treatments. Plasma samples were kept frozen until the time of analysis. Valproic acid plasma concentrations were determined by E.M.I.T. assay method.

The table below represents average values of valproic acid concentration in plasma found for the three products.

| Time (Hours) | A mcg/ml | (± S.E.) | B mcg/ml | (± S.E.) | C mcg/ml | (± S.E.) |
|---|---|---|---|---|---|---|
| 0.25 | 49.39 | (6.98) | 13.56 | (3.43) | 0.00 | |
| 0.50 | 64.17 | (7.35) | 39.83 | (4.86) | 0.00 | |
| 0.75 | 68.94 | (4.81) | 62.33 | (9.80) | 0.00 | |
| 1.00 | 61.94 | (3.80) | 72.78 | (8.69) | 0.00 | |
| 1.50 | 62.39 | (3.26) | 76.83 | (6.16) | 8.00 | (4.32) |
| 2.00 | 60.88 | (3.52) | 72.61 | (4.91) | 14.44 | (6.32) |
| 3.00 | 51.56 | (4.26) | 65.17 | (4.23) | 48.56 | (8.64) |
| 4.00 | 48.38 | (2.71) | 58.39 | (4.16) | 57.78 | (4.06) |

-continued

| Time (Hours) | A mcg/ml | (± S.E.) | B mcg/ml | (± S.E.) | C mcg/ml | (± S.E.) |
|---|---|---|---|---|---|---|
| 6.00 | 42.00 | (2.44) | 49.28 | (4.82) | 56.72 | (4.26) |
| 8.00 | 34.13 | (2.12) | 43.11 | (4.55) | 47.57 | (2.32) |
| 10.00 | 32.14 | (2.88) | 38.22 | (3.87) | 45.11 | (3.22) |
| 12.00 | 26.17 | (3.92) | 31.78 | (3.22) | 37.56 | (2.77) |
| 25.00 | 12.89 | (1.95) | 16.44 | (2.19) | 17.11 | (1.35) |
| 36.00 | 5.50 | (1.49) | 7.50 | (1.59) | (6.80) | (0.67) |

Product A: Valproic acid syrup 250 mg/5 ml
Product B: Valproic acid 500 mg tablets of this invention
Product C: Sodium valproate 300 mg, enteric coated tablets.

The table below represents the pharmacokinetic parameters calculated for each of three products.

| Product* | tmax (hrs) | Cmax (mcg/ml) | AUC$_{0 \to \infty}$ (mcgh ml$^{-1}$) | Bioavailability (%) |
|---|---|---|---|---|
| A (500) | 0.75 | 68.94 | 972.86 | 100.0 |
| B (500) | 1.50 | 76.83 | 1,148.28 | 118.0 |
| C (520) | 4.00 | 57.78 | 1,037.44 | 106.6 |

(*) Number in parenthesis is valproic acid, mg/dose.

The result of this experiment clearly shows that the tablets prepared according to this invention when orally administered achieve valproic acid blood levels comparable to those reached after the administration of a solution of valproic acid (syrup) at the same dose.

What is claimed is:

1. A tablet comprising:
   a) 55 to 65 weight percent valproic acid,
   b) 10 to 25 weight percent of a filler selected from the group of clays and alkaline earth metal oxides,
   c) 10 to 20 weight percent of a material selected from the group of polysaccharides having disintegrant properties,
   d) 3 to 6 weight percent of binder materials selected from the group consisting of hydrophilic gel forming polymers, and
   e) 0.5 to 1.2 weight percent lubricant materials selected from the group of talc, fatty acids and salts of fatty acids.

2. The tablet of claim 1 comprising:
   a) 55 to 65 weight percent valproic acid,
   b) 10 to 25 weight percent of a filler selected from the group of magnesium oxide, aluminium oxide, magnesium and aluminium silicates, calcium oxide, and zinc oxide,
   c) 10 to 20 weight percent disintegrant selected from the group of corn starch and potato starch,
   d) 3 to 6 weight percent binder selected from hydrophilic cellulose gums, polyvinylpyrrolidone and xanthan gum, and
   e) 0.5 to 1.2 weight percent lubricant selected from the group of talc, magnesium and calcium stearate.

3. The tablet of claim 1 wherein the filler is magnesium oxide.

4. The tablet of claim 1 wherein the disintegrant is corn starch.

5. The tablet of claim 1 wherein the binder is a combination of polyvinylpyrrolidone and sodium carboxymethylcellulose.

6. The tablet of claim 5 wherein the polyvinylpyrrolidone and the sodium carboxymethylcellulose are combined in a 3:1 ratio.

7. The tablet of claim 1 wherein the lubricant is magnesium or calcium stearate.

8. The tablet of claim 1 comprising:
   a) 60 weight percent of valproic acid,
   b) 20 weight percent of magnesium oxide,
   c) 15 weight percent corn or potato starch,
   d) 3 weight percent polyvinylpyrrolidone,
   e) 1 weight percent sodium carboxymethylcellulose, and
   f) 0.8 weight percent magnesium stearate.

9. A method for compounding valproic acid as a moisture stable powder comprising:
   (a) mixing valproic acid and ethyl alcohol in a 5:1 ratio,
   (b) slowly adding a clay of an alkaline earth metal oxide to the mixture resulting from (a) while mixing,
   (c) drying the wet mass resulting from (b),
   (d) sizing the dried material resulting from (c),
   (e) adding a suitable disintegrant to the product of (d) and mixing,
   (f) thereafter wet granulating the mixture resulting from (e) with an alcoholic solution of a hydrophilic water soluble polymer,
   (g) drying the wet granulate and combining with lubricant, and
   (h) thereafter compressing the resultant lubricant/granulate mixture.

* * * * *